United States Patent
Abe et al.

(10) Patent No.: US 7,722,540 B2
(45) Date of Patent: May 25, 2010

(54) ULTRASONIC IMAGE PROCESSING APPARATUS, ULTRASONIC DIAGNOSTIC APPARATUS, AND ULTRASONIC IMAGE PROCESSING PROGRAM

(75) Inventors: Yasuhiko Abe, Otawara (JP); Tetsuya Kawagishi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 726 days.

(21) Appl. No.: 11/457,319

(22) Filed: Jul. 13, 2006

(65) Prior Publication Data

US 2007/0038087 A1    Feb. 15, 2007

(30) Foreign Application Priority Data

Jul. 15, 2005    (JP)    ............... 2005-207687

(51) Int. Cl.
*A61B 8/00* (2006.01)
(52) U.S. Cl. ...................................... 600/443; 600/447
(58) Field of Classification Search ................. 600/443, 600/447
See application file for complete search history.

(56) References Cited

U.S. PATENT DOCUMENTS

| | | | | |
|---|---|---|---|---|
| 4,930,513 A | * | 6/1990 | Mayo et al. ................... | 600/455 |
| 5,000,184 A | * | 3/1991 | Bonnefous ................... | 600/455 |
| 5,390,677 A | | 2/1995 | Ferrera et al. | |
| 5,899,863 A | * | 5/1999 | Hatfield et al. ............... | 600/443 |
| 6,099,471 A | | 8/2000 | Torp et al. | |
| 6,210,168 B1 | * | 4/2001 | Aiger et al. ................... | 434/262 |
| 6,234,968 B1 | * | 5/2001 | Sumanaweera et al. ..... | 600/443 |
| 6,638,221 B2 | * | 10/2003 | Abe et al. ................... | 600/437 |
| 6,735,463 B2 | * | 5/2004 | Izatt et al. ................... | 600/476 |
| 2003/0013963 A1 | | 1/2003 | Bjaerum et al. | |
| 2003/0097068 A1 | * | 5/2003 | Hossack et al. ............... | 600/443 |

FOREIGN PATENT DOCUMENTS

CN    1509691 A    7/2004
JP    2003-175041    6/2003

OTHER PUBLICATIONS

P. R. Hoskins, et al., "Colour Ultrasound Imaging of Blood Flow and Tissue Motion", The British Journal of Radiology, XP-002404496, vol. 70, No. 837, Sep. 1997, pp. 878-890.

(Continued)

*Primary Examiner*—Long V Le
*Assistant Examiner*—Saurel J Selkin
(74) *Attorney, Agent, or Firm*—Oblon, Spivak, McClelland, Maier & Neustadt, L.L.P.

(57) ABSTRACT

When a two-dimensional tomogram is to be displayed, motion information associated with a direction orthogonal to the tomogram is colored and mapped on the tomogram to be visualized by using the volume data of a TSI image. For example, a mapping image is generated by color-mapping shortening information at each point on a cardiac tissue on a short axis view by using the volume data of the TSI image. Superimposing and displaying the mapping image on the original short axis view makes it possible to simultaneously observe the shortening information even while a short axis view is obtained and observed.

20 Claims, 17 Drawing Sheets

OTHER PUBLICATIONS

Jørgen Mæhle, et al., "Three-Dimensional Echocardiography for Quantitative Left Ventricular Wall Motion Analysis: a Method for Reconstruction of Endocardial Surface and Evaluation of Regional Dysfunction", Echocardiography: a Journal of CV Ultrasound & Allied Tech, XP-008024521, vol. 11, No. 4, Jul. 1994, pp. 397-408.

U.S. Appl. No. 12/109,805, filed Apr. 25, 2008, Abe, et al.

U.S. Appl. No. 12/548,816, filed Aug. 27, 2009, Abe.

J.A. Jensen, et al., "Method for Real-Time Three Dimensional Vector Velocity Imaging", 2003 IEEE Ultrasonics Symposium Proceedings, Honolulu, Hawaii, vol. 2, Oct. 5, 2003, pp. 1582-1585, XP010701790 ISBN: 978-0-7803-7922-0.

* cited by examiner

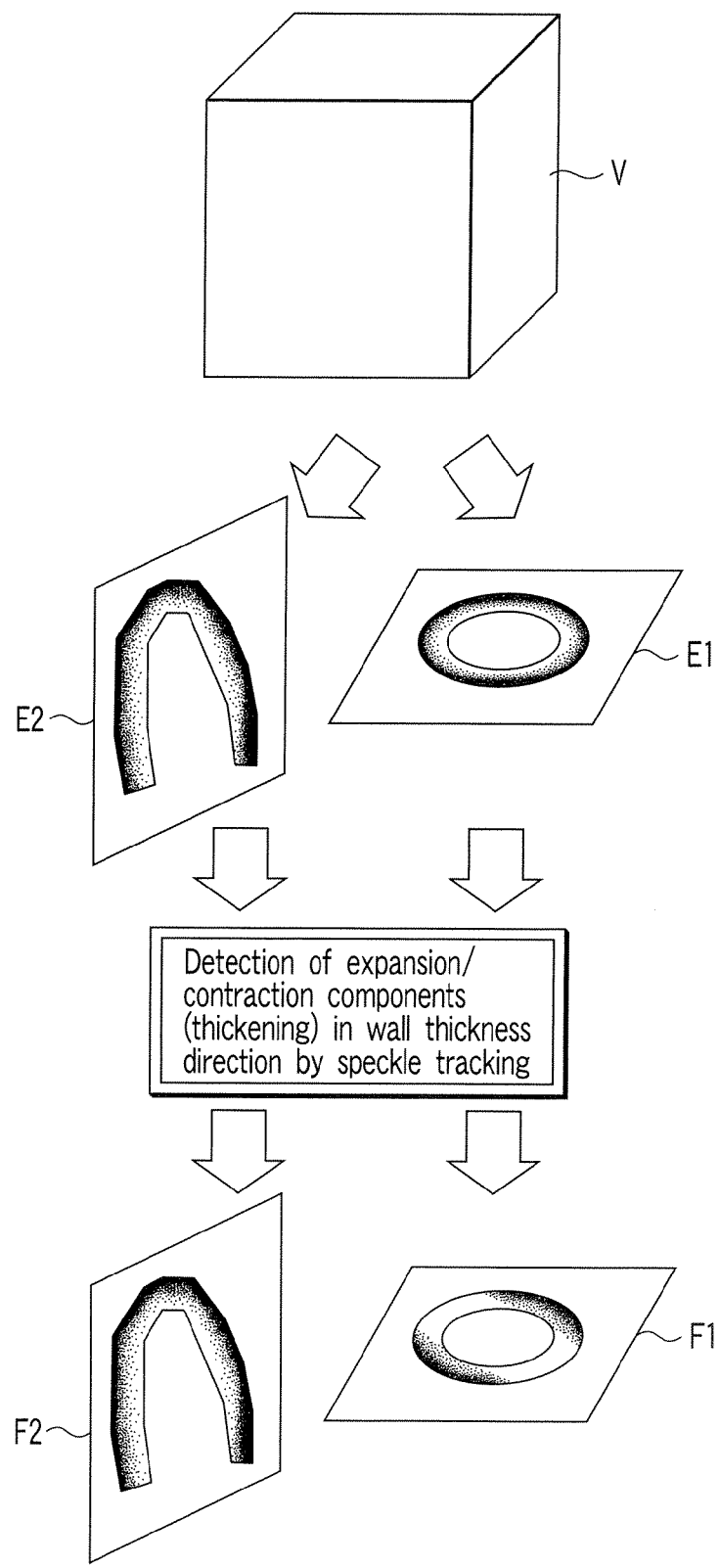
F I G. 15

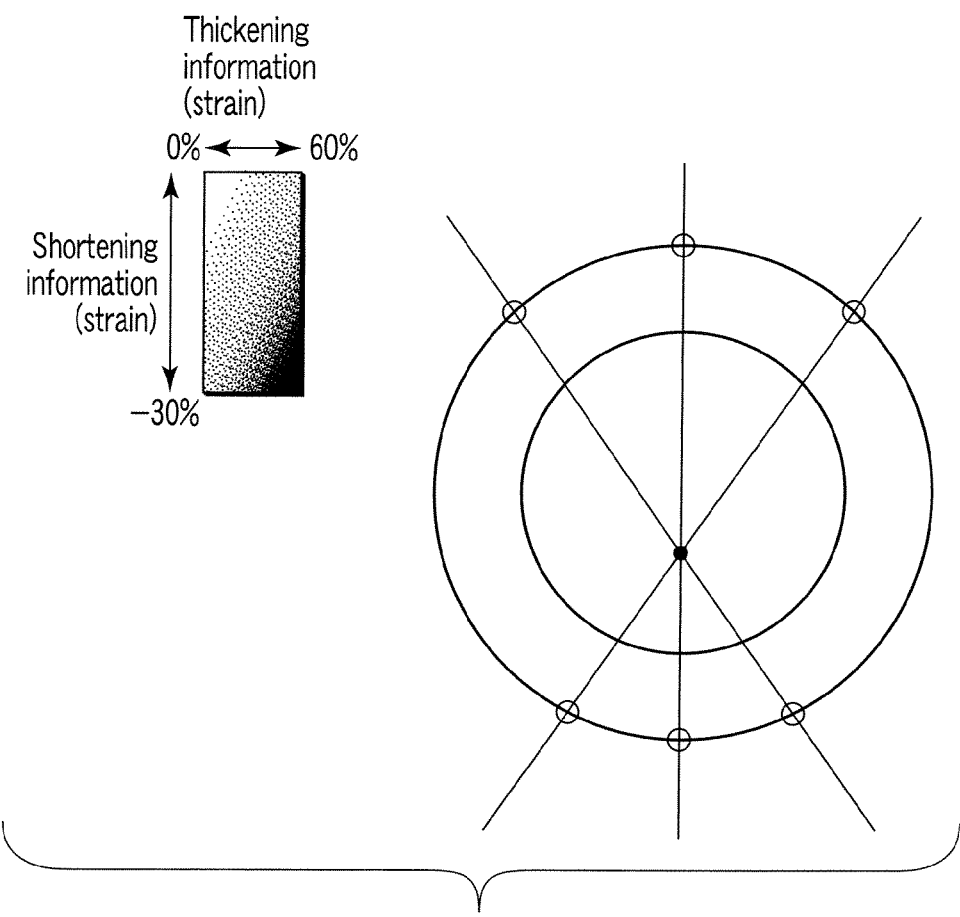
F I G. 17
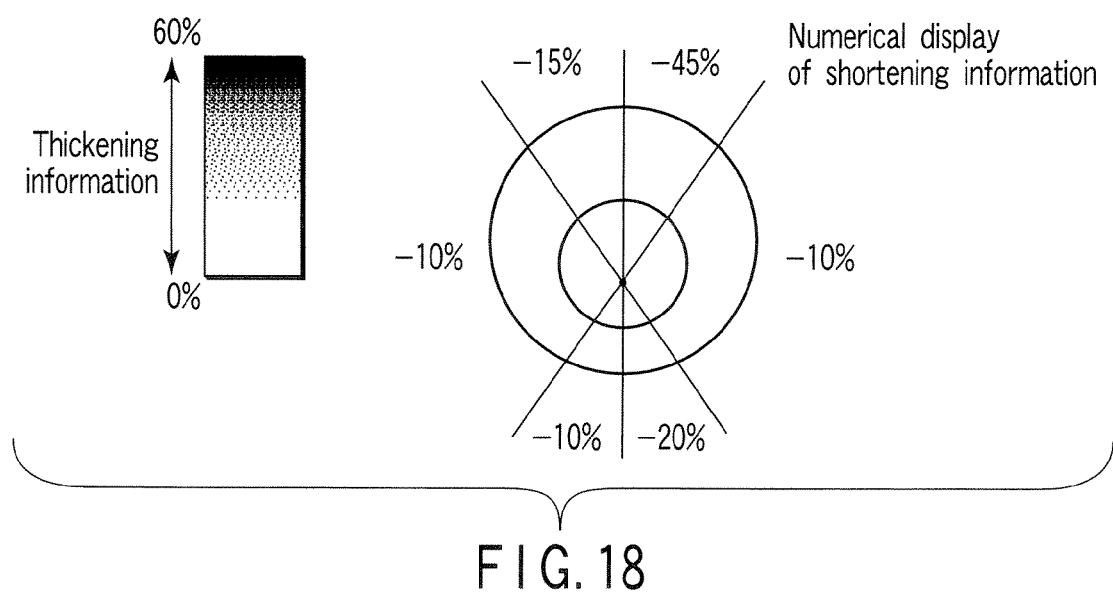
F I G. 18

ULTRASONIC IMAGE PROCESSING APPARATUS, ULTRASONIC DIAGNOSTIC APPARATUS, AND ULTRASONIC IMAGE PROCESSING PROGRAM

CROSS-REFERENCE TO RELATED APPLICATIONS

This application is based upon and claims the benefit of priority from prior Japanese Patent Application No. 2005-207687, filed Jul. 15, 2005, the entire contents of which are incorporated herein by reference.

BACKGROUND OF THE INVENTION

1. Field of the Invention

The present invention relates to the visualization of a heart by using the TSI (Tissue Strain Imaging) method and, more particularly, to the mapping of the shortening information of the heart in the long axis direction in a contraction phase to a short axis image or the mapping of the thickening information of the heart in the cardiac wall thickness direction to a short axis image.

2. Description of the Related Art

In general, with regards to a living tissue such as cardiac muscle, it is very important for the diagnosis of the tissue to objectively and quantitatively evaluate the motion or function of the tissue. In image diagnosis using an ultrasonic image processing apparatus, various quantitative evaluation methods have been tried mainly for heart cases. For example, it is known that the normal cardiac muscle thickens in the wall thickness direction (short axis), and shortens in the long axis direction in a contraction phase. It is generally said that the motion directions of thickening and shortening are perpendicular to each other and exhibit different mechanisms. It is suggested that evaluating the myocardial wall motion by observing these motions makes it possible to support diagnosis associated with a heart disease such as myocardial infarction.

In a conventional ultrasonic diagnostic apparatus, however, the following problems arise. While a short axis view is obtained and observed, no biometric information perpendicular to a scanning plane of the short axis view can be acquired due to the characteristics of the ultrasonic diagnostic apparatus. Therefore, shortening information cannot be simultaneously expressed. In addition, while a apical long axis approach is obtained and observed by, for example, the tissue Doppler method, thickening information cannot be simultaneously expressed because of a Doppler angle limitation.

BRIEF SUMMARY OF THE INVENTION

The present invention has been made in consideration of the above situation, and has as its object to provide an ultrasonic image processing apparatus, ultrasonic diagnostic apparatus, and ultrasonic image processing program which allow simultaneous observation of shortening information even while a short axis view is obtained and observed, and allow simultaneous observation of thickening information even while a long axis view is obtained and observed.

According to an aspect of the present invention, there is provided an ultrasonic diagnostic apparatus comprising a motion information generating unit which generates motion information of a tissue which includes a component in a first direction, a two-dimensional image generating unit which generates a two-dimensional image associated with a plane which is not parallel to the first direction, a mapping image generating unit which generates a mapping image by mapping the motion information on the two-dimensional image, and a display unit which displays the mapping image.

According to another aspect of the present invention, there is provided an ultrasonic diagnostic apparatus comprising a calculation unit which calculates a parameter associated with three-dimensional motion of a tissue, an image generating unit which generates a two-dimensional image from three-dimensional data, and a display unit which displays the calculated parameter together with the generated two-dimensional image.

According to yet another aspect of the present invention, there is provided an ultrasonic image processing method comprising generating motion information of a tissue which includes a component in a first direction, generating a two-dimensional image associated with a plane which is not parallel to the first direction, generating a mapping image by mapping the motion information on the two-dimensional image, and displaying the mapping image.

According to yet another aspect of the present invention, there is provided an ultrasonic image processing method comprising calculating a parameter associated with three-dimensional motion of a tissue, generating a two-dimensional image from three-dimensional data, and displaying the calculated parameter together with the generated two-dimensional image.

BRIEF DESCRIPTION OF THE SEVERAL VIEWS OF THE DRAWING

FIG. 15 is a view for explaining the concept of mapping processing in the second embodiment;

FIG. 17 is a view showing a modification of the display form of thickening information and shortening information in a mapping image;

FIG. 18 is a view showing a modification of the display form of thickening information and shortening information in a mapping image;

DETAILED DESCRIPTION OF THE INVENTION

Figure 1:
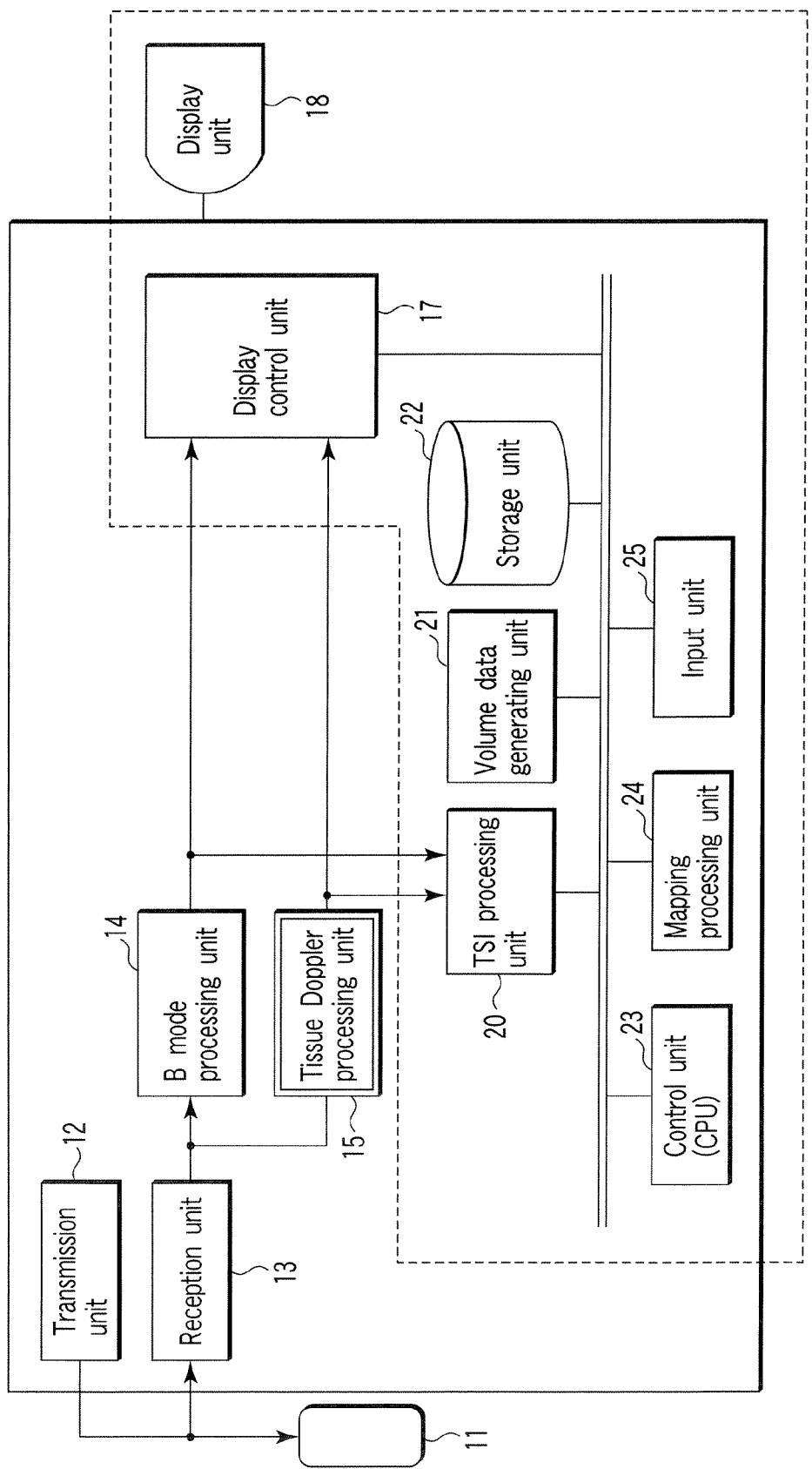
FIG. 1 is a block diagram showing the arrangement of an ultrasonic diagnostic apparatus 10 according to the first embodiment.

The first and second embodiments of the present invention will be described below with reference to the views of the accompanying drawing. Note that the same reference numerals denote constituent elements having substantially the same functions and arrangements, and a repetitive description will be made only when required.

Note that each embodiment described above will exemplify a case wherein the technical idea of the present invention is applied to an ultrasonic diagnostic apparatus. However, the present invention is not limited to this, and the technical idea can be applied to an ultrasonic image processing apparatus such as a workstation or personal computer.

The respective constituent elements according to this embodiment, and more particularly, a TSI processing unit 20, volume data generating unit 21, mapping processing unit 24, and tracking processing unit 27 (see FIGS. 1 and 14) which will be described later can also be implemented by installing software programs for executing processes similar to those executed by the respective constituent elements in a computer such as a workstation, an ultrasonic diagnostic apparatus having a computer function, or the like, and loading them into a memory. In this case, the programs which can cause the computer to execute the corresponding techniques can be distributed by being stored in recording media such as magnetic disks (floppy disks, hard disks, and the like), optical disks (CD-ROMs, DVDs, and the like), and semiconductor memories.

First Embodiment

FIG. 1 is a block diagram showing the arrangement of an ultrasonic diagnostic apparatus 10 according to the first embodiment. The ultrasonic diagnostic apparatus 10 comprises an ultrasonic probe 11, a transmission unit 12, a reception unit 13, a B mode processing unit 14, a tissue Doppler processing unit 15, a display control unit 17, a display unit 18, the TSI processing unit 20, the volume data generating unit 21, a storage unit 22, a control unit (CPU) 23, the mapping processing unit 24, and an input unit 25. Note that when the present invention is applied to the ultrasonic processing apparatus, the constituent elements of the apparatus are those enclosed by the dotted line in FIG. 1.

The ultrasonic probe 11 generates ultrasonic waves on the basis of a driving signal from the transmission unit 12, and includes a plurality of piezoelectric vibrators which convert reflected waves from a subject to be examined into electrical signals, a matching layer provided for the piezoelectric vibrators, a backing member which prevents ultrasonic waves from propagating backward from the piezoelectric vibrators, and the like. When ultrasonic waves are transmitted from the ultrasonic probe 11 to the subject, various harmonic components are generated due to the nonlinearity of a living tissue upon propagation of ultrasonic waves. Fundamental waves and harmonic components constituting transmission ultrasonic waves are scattered backward by acoustic impedance boundaries of a tissue in a living body, micro-scattering, and the like, and are received as reflected waves (echoes) by the ultrasonic probe 11.

The transmission unit 12 includes a delay circuit, a pulser circuit, and the like (not shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The transmission unit 12 applies a driving pulse to each vibrator so as to form an ultrasonic beam toward a predetermined scan line at the timing based on this rate pulse.

The reception unit 13 includes an amplifier circuit, an A/D converter, an adder, and the like (not shown). The amplifier circuit amplifies an echo signal received through the probe 11 for each channel. The A/D converter gives the amplified echo signals delay times necessary to determine reception directivities. The adder then performs addition processing for the signals. With this addition, an ultrasonic echo signal corresponding to a predetermined scan line is generated.

The B mode processing unit 14 performs envelope detection processing for the ultrasonic echo signal received from the reception unit 13 to generate a B mode signal corresponding to the amplitude intensity of the ultrasonic echo.

The tissue Doppler processing unit 15 performs quadrature detection processing, autocorrelation processing, and the like for the echo signal received from the reception unit 13, and obtains a tissue Doppler signal corresponding to the velocity, variance, and power of the tissue which moves in the subject on the basis of the Doppler shift component of the ultrasonic echo signal having undergone delay/addition processing.

The display control unit 17 generates a B mode ultrasonic image representing a dimensional distribution associated with a predetermined slice of the B mode signal. The display control unit 17 generates a tissue Doppler ultrasonic image representing the two-dimensional distribution of velocities, variances, and power values which is associated with a predetermined slice on the basis of the tissue Doppler signal. The display control unit 17 generates a superimposed image of a B mode ultrasonic image and a tissue Doppler ultrasonic image, a superimposed image of a B mode ultrasonic image and an image associated with the motion information of the tissue, or the like, as needed. In this case, the motion information of the tissue is physical information which can be acquired in association with the motion of the tissue, e.g., the strain, strain rate, displacement, or velocity of the tissue.

Images including such tissue motion information will be generically termed "TSI images" hereinafter.

The display unit 18 displays morphological information and blood flow information in the living body as images on the basis of video signals from the display control unit 17. When a contrast medium is used, the display unit 18 displays such an image as a luminance image or a color image on the basis of the spatial distribution of the contrast medium, i.e., a quantitative information amount obtained by obtaining an area where a blood flow or blood exists.

The TSI processing unit 20 generates a TSI image associated with the strain of the tissue by executing TSI processing by using the B mode signal output from the B mode processing unit 14, the Doppler signal output from the tissue Doppler processing unit 15, and the B mode image data, Doppler image data, velocity distribution image, and the like which are stored in the storage unit 22. In this case, the velocity distribution image is an image representing velocities at a plurality of positions on a diagnosis target tissue for each time phase.

The volume data generating unit 21 executes spatial interpolation processing by using TSI images associated with a plurality of slices associated with a predetermined target which are generated by the TSI processing unit 20 as needed. With this operation, the volume data of the TSI image associated with the predetermined target is generated.

The storage unit 22 stores ultrasonic image data (e.g., tissue image data obtained in the tissue Doppler mode, the M mode, or the like) corresponding to each time phase, a velocity distribution image corresponding to each time phase which is generated by the TSI processing unit 20, a TSI image, and the like. In addition, the storage unit 22 stores the volume data of the TSI image generated by the volume data generating unit 21, as needed. Note that the ultrasonic image data stored in the storage unit 22 may be so-called raw image data before scan conversion.

The control unit (CPU) 23 has a function of an information processing apparatus (computer), and statically or dynamically controls this ultrasonic diagnostic apparatus.

The mapping processing unit 24 performs mapping processing of mapping shortening information on a selected short axis slice on the basis of the volume data of the TSI image generated by the volume data generating unit 21. The mapping processing unit 24 performs mapping processing of mapping thickening information on a selected long axis slice on the basis of the volume data of the TSI image.

The input unit 25 is connected to the apparatus body and includes a mouse, trackball, mode switch, keyboard, and the like which are used to input, to the apparatus body, various instructions from the operator, an instruction to set a region of interest (ROI), various image quality setting instructions, and the like.

(Tissue Strain Imaging: TSI)

A tissue strain imaging method as a technique which is a premise of this embodiment will be briefly described next. This tissue strain imaging method is designed to visualize parameters such as a local displacement, strain, and the like which are obtained as tissue motion information by integrating signals originating from velocity information while tracking a tissue position upon movement. According to this technique, images associated with the local myocardial strain and displacement of the heart can be generated and displayed, thereby supporting the analysis of temporal changes in image output value in a local area.

In the tissue strain imaging method, when, for example, thickening is to be observed by using a short axis view, the concept and settings of a contraction motion field directed to a contraction center are used to detect and visualize a component associated with thickening by angle correction. In addition, according to the tissue strain imaging method, the contraction center position is temporally moved in consideration of the translational motion (also called "translation") of the overall heart so as to allow the method to be applied to a motion field which is temporally variable. Therefore, this method can follow variations in contraction center position due to translational motion. The details of the tissue strain imaging method are described in, for example, Jpn. Pat. Appln. KOKAI Publication No. 2003-175041.

Note that in this tissue strain imaging method, velocity distribution images associated with a plurality of time phases are required. The velocity distribution images can be obtained from two-dimensional or three-dimensional ultrasonic image data associated with a plurality of time phases which are acquired by the tissue Doppler method or performing pattern matching processing for a plurality of two-dimensional or three-dimensional tissue images associated with a plurality of time phases which are acquired in the B mode or the like. In this embodiment, for the sake of concrete description, assume that a two-dimensional velocity distribution image generated by performing pattern matching processing for B mode images in the respective time phases is used. However, the present invention is not limited to this. For example, a two-dimensional or three-dimensional velocity distribution image generated by the tissue Doppler method may be used.

(Acquisition of Volume Data)

In mapping processing to be described later, for example, the volume data of a TSI image associated with a diagnosis target (the heart in this case) is required. For this reason, the ultrasonic diagnostic apparatus 10 has several functions for the acquisition of the volume data of a TSI image. These functions will be described below.

Figure 2:
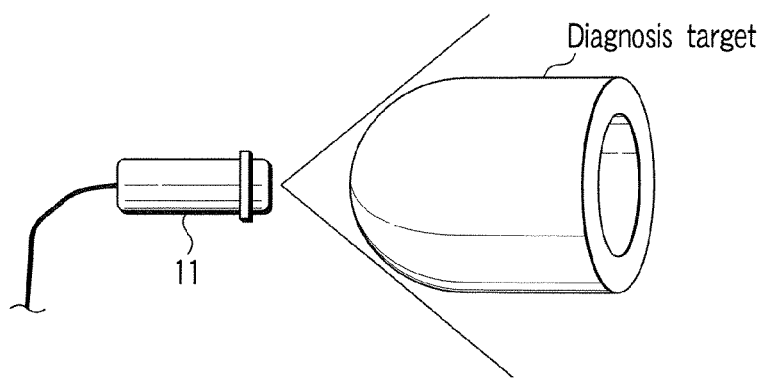
FIG. 2 is a view showing the first technique for the acquisition of the volume data of a TSI image.

FIG. 2 is a view showing the first technique for the acquisition of the volume data of a TSI image, and more specifically, a technique of acquiring volume data by volume scanning in a three-dimensional area actually including a diagnosis region. That is, volume data can be acquired by performing volume scanning in a three-dimensional area actually including a diagnosis region using a two-dimensional array probe (i.e., a probe having ultrasonic transducers arranged in the form of a matrix) or by performing volume scanning which is performed by causing a one-dimensional array probe to mechanically or manually perform tilting operation. Volume data can be acquired for each time phase by continuously performing volume scanning. Performing TSI processing using these volume data makes it possible to acquire the volume data of a TSI image associated with a diagnosis target for each time phase.

Figure 3:
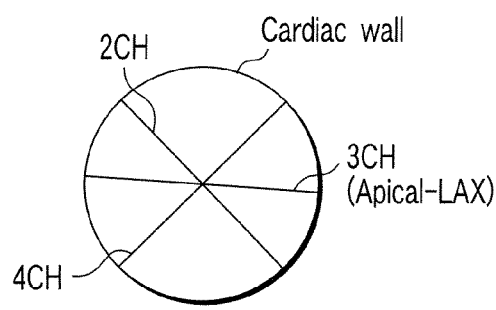
FIG. 3 is a view for explaining the second technique for the acquisition of volume data.
Figure 4:
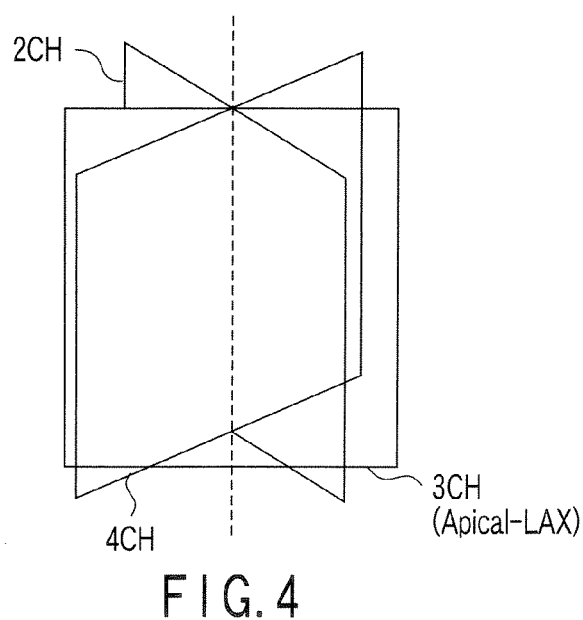
FIG. 4 is a view for explaining the second technique for the acquisition of volume data.

FIGS. 3 and 4 show the second technique for the acquisition of volume data. As shown in FIGS. 3 and 4, for example, three long axis tomograms of a 2-chamber view (2-CH), apex long axis view (3-CH), and 4-chamber view (4-CH) are acquired for each time phase, and TSI processing using these tomograms is performed. The volume data of a TSI image associated with a diagnosis target can be acquired for each time phase by interpolation processing for a TSI image associated with the three obtained long axis tomograms.

Figure 5:
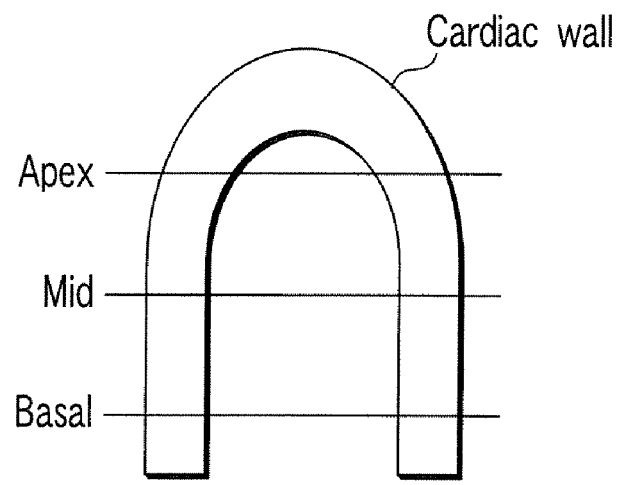
FIG. 5 is a view for explaining the third technique for the acquisition of volume data.
Figure 6:
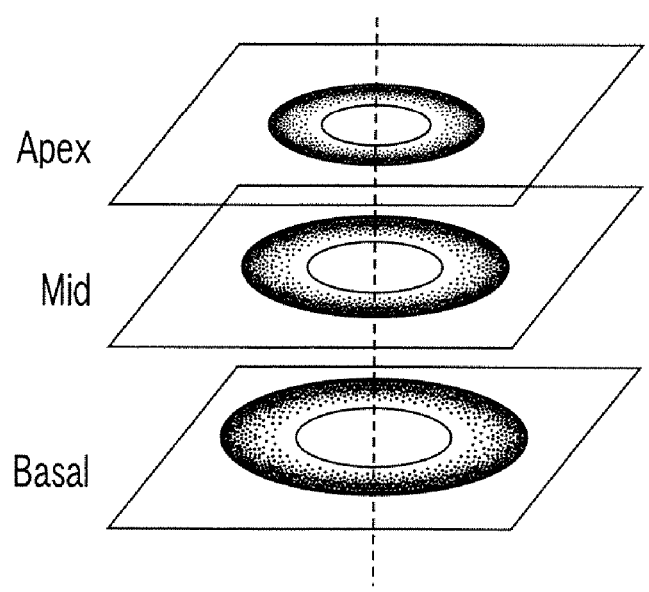
FIG. 6 is a view for explaining the third technique for the acquisition of volume data.

FIGS. 5 and 6 show the third technique for the acquisition of volume data. As shown in FIGS. 5 and 6, for example, three tomograms at a basal level (Basal), middle level (Mid), and apex level (Apex) are acquired for each time phase, and TSI processing is performed by using them. The volume data of a TSI image associated with a diagnosis target can be acquired for each time phase by performing interpolation processing for a TSI image associated with the three obtained short axis tomograms.

When the first technique is compared with the second and third techniques, the second and third techniques may sometimes be inferior in spatial resolution to the first technique but superior in time resolution to the first technique depending on the specifications of the apparatus. In such a case, it is necessary to determine which technique should be used in accordance with the purpose of diagnosis. The second and third techniques have exemplified the interpolation processing based on three slices. However, the number of slices to be used is not limited to this. The number of tomograms to be acquired by imaging (based on interpolation processing) can be arbitrarily set as long as interpolation can be performed.

(Orthogonal Mapping Processing)

The orthogonal mapping function which the ultrasonic diagnostic apparatus 10 has will be described next. With this function, when a two-dimensional tomogram is to be displayed, motion information associated with a direction orthogonal to the tomogram is visualized by coloring the tomogram and performing mapping (color mapping) using the volume data of a TSI image. This makes it possible to observe motion in a direction along a scanning line on a tomogram and motion associated with a direction orthogonal to the tomogram on the same two-dimensional tomogram.

Figure 7:
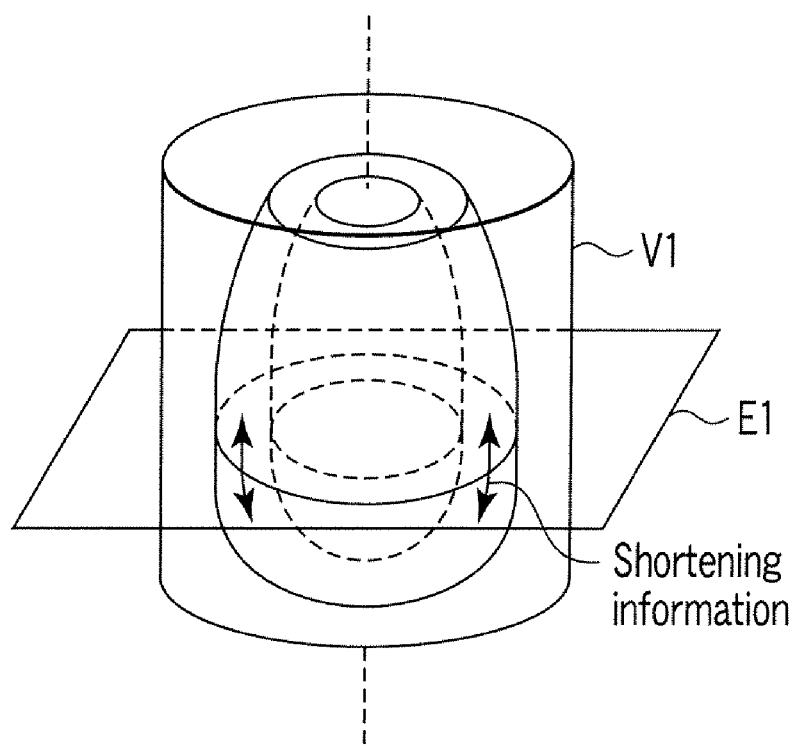
FIG. 7 is a view showing an example of a conceptual view for explaining an orthogonal mapping function.
Figure 8:
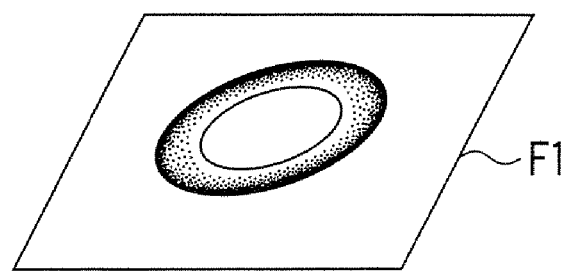
FIG. 8 is a view showing an example of a conceptual view for explaining the orthogonal mapping function.

FIGS. 7 and 8 show an example of a conceptual view for explaining the orthogonal mapping function. Assume that as shown in FIG. 7, volume data V1 associated with a diagnosis target has been generated by interpolation processing using a TSI image associated with three different long axis tomograms (see FIGS. 3 and 4). A mapping image F1 is generated by designating an arbitrary short axis slice E1 with respect to the volume data V1 and color-converting shortening information at each point on the tissue on the short axis slice E1 with a luminance corresponding to the magnitude of the strain by using the volume data V1. Displaying the mapping image F1 while superimposing it on a general ultrasonic image of the short axis slice E1 makes it possible to observe shortening information on the short axis tomogram.

Figure 9:
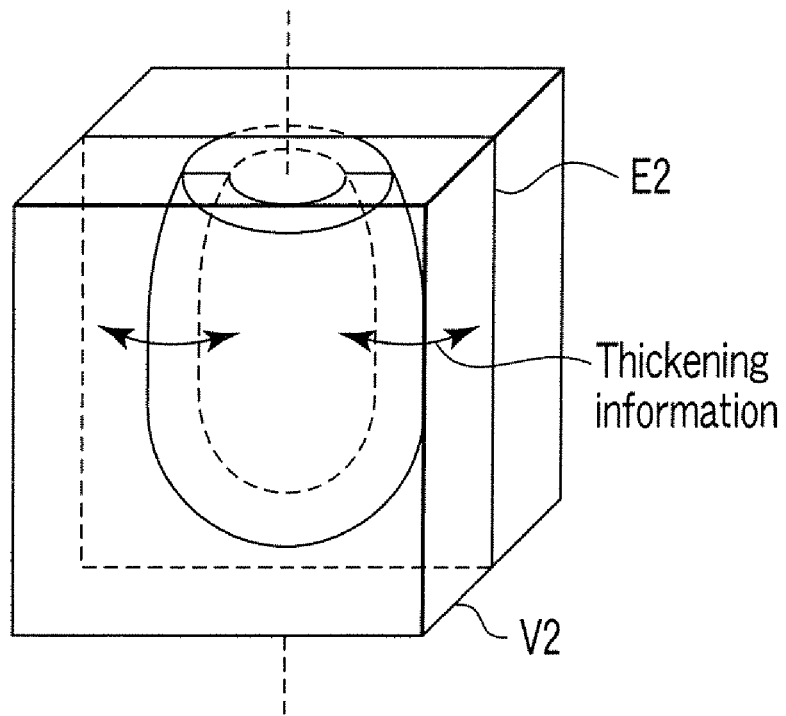
FIG. 9 is a view showing another example of a conceptual view for explaining the orthogonal mapping function.
Figure 10:
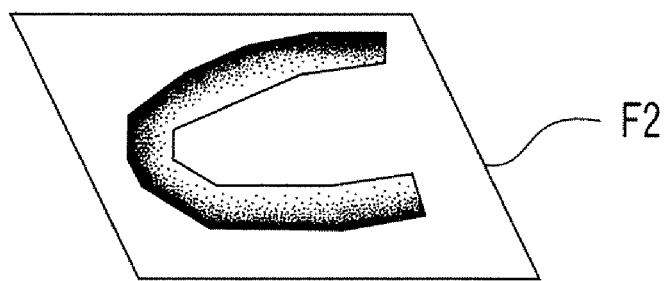
FIG. 10 is a view showing still another example of a conceptual view for explaining the orthogonal mapping function.

FIGS. 9 and 10 are other examples of conceptual views for explaining the orthogonal mapping function. Assume that as shown in FIG. 9, volume data V2 associated with a diagnosis target has been generated by interpolation processing using a TSI image associated with three different short axis tomograms (see FIGS. 5 and 6). A mapping image F2 is generated by designating an arbitrary long axis slice E2 with respect to the volume data V2 and color-converting thickening information at each point on the tissue on the long axis slice E2 with a luminance corresponding to the magnitude of the strain by using the volume data V2. Displaying the mapping image F2 while superimposing it on a general ultrasonic image of the short axis slice E2 makes it possible to observe thickening information on the long axis tomogram.

Figure 11:
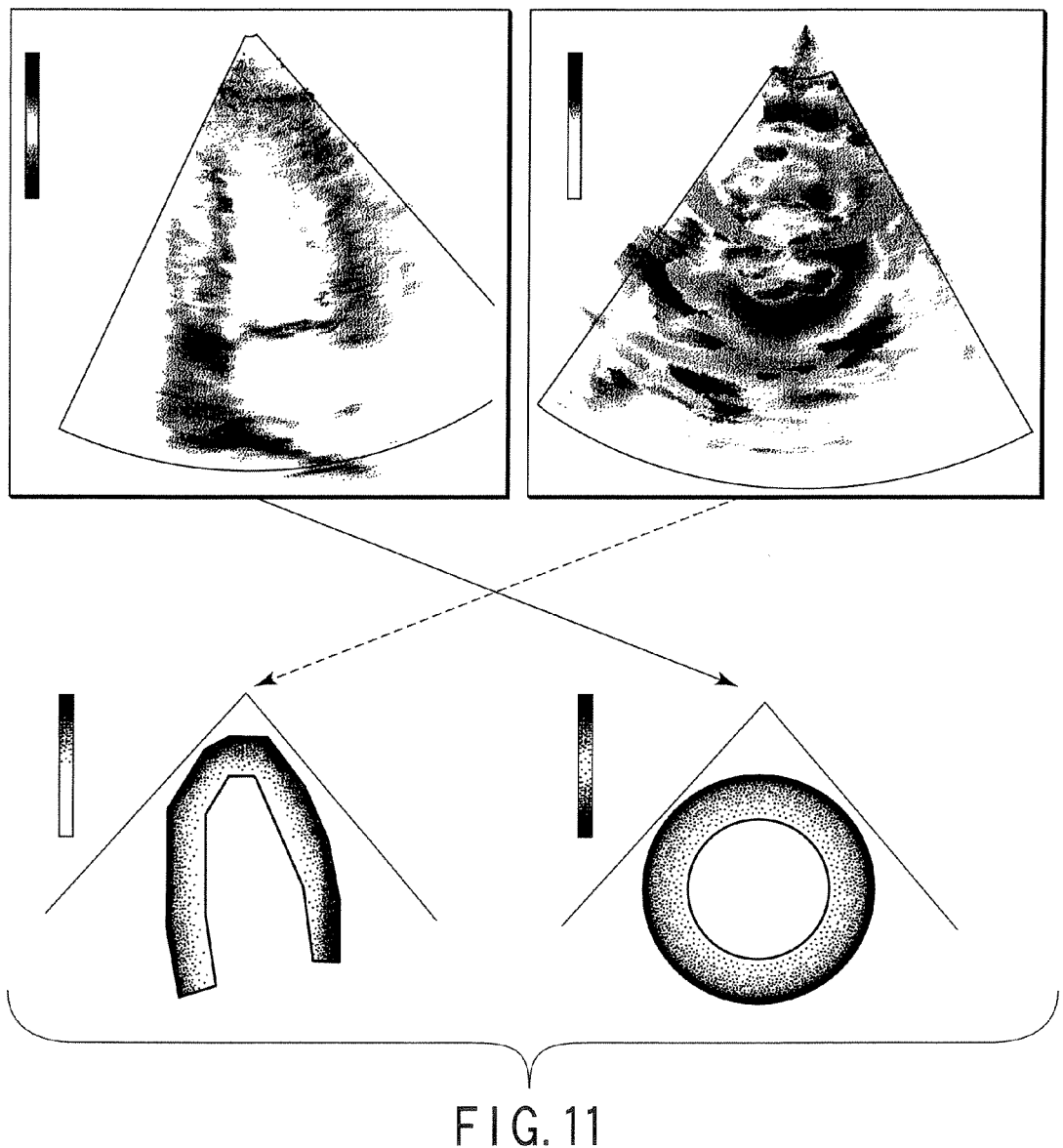
FIG. 11 is a conceptual view for explaining the orthogonal mapping function.

The orthogonal mapping processing in each example described above is mapping using volume data associated with a TSI image of a diagnosis target. Volume data associated with this TSI image can be acquired by the above technique including interpolation processing. According to this technique, therefore, shortening information can be visualized on a short axis (long axis) tomogram by being mapped thereon as indicated by the lower part of FIG. 11 by only obtaining a plurality of long axis (a plurality of short axis) tomograms as indicted by the upper part of FIG. 11.

Example 1

The operation of the ultrasonic diagnostic apparatus 10 in orthogonal mapping processing will be described next. Example 1 will exemplify a case wherein the shortening information of a strain on a short axis tomogram is mapped.

Figure 12:
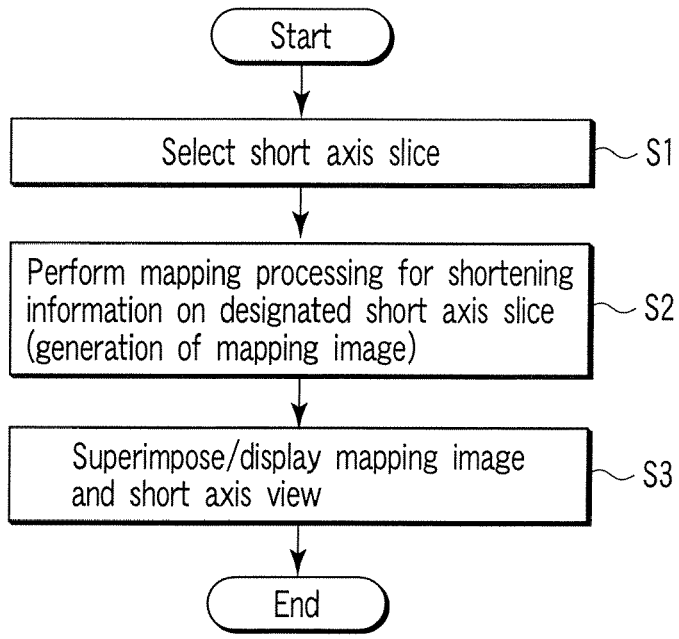
FIG. 12 is a flowchart showing the flow of each process executed in orthogonal mapping processing according to Example 1.

FIG. 12 is a flowchart showing the flow of each process executed in orthogonal mapping processing according to this example. As shown in FIG. 12, first of all, a short axis slice at an arbitrary (desired) position is selected with respect to the volume data of a TSI image (step S1).

The mapping processing unit 24 acquires shortening information in the long axis direction which is associated with each position of a tissue on a designated short axis slice by using the volume data, and performs color mapping of the information such that a strain intensity is made to correspond to its gray level. With this mapping processing, a mapping image is generated (step S2).

The display control unit 17 then displays a general ultrasonic image (short axis view) associated with the designated short axis slice and the generated mapping image on the screen of the display unit 18 while superimposing them (step S3).

Example 2

The operation of the ultrasonic diagnostic apparatus 10 in orthogonal mapping processing will be described next. Example 2 will exemplify a case wherein the thickening information of a strain is mapped on a long axis view.

Figure 13:
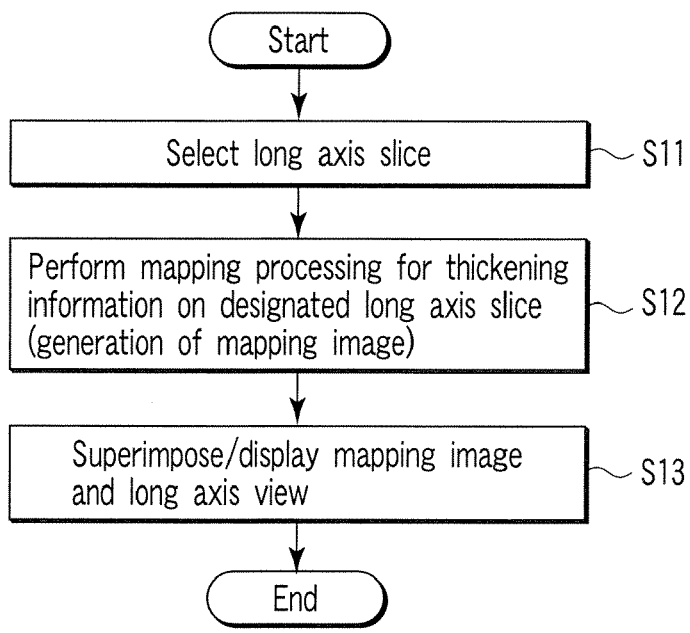
FIG. 13 is a flowchart showing the flow of each process executed in orthogonal mapping processing according to Example 2.

FIG. 13 is a flowchart showing the flow of each process to be executed in orthogonal mapping processing according to this example. As shown in FIG. 13, first of all, a long axis slice at an arbitrary (desired) position is selected with respect to the volume data of a TSI image (step S11).

The mapping processing unit 24 then acquires expansion (thickening information) in a short axis direction which is associated with each position on a tissue exiting on the designated long axis slice, and performs color mapping of the acquired information such that the intensity of a strain is made to correspond to its gray level. With this mapping processing, a mapping image is generated (step S12).

The display control unit 17 then displays a general ultrasonic image (long axis view) associated with the designated long axis slice and the generated mapping image on the screen of the display unit 18 while superimposing them (step S13).

According to the above arrangement, the following effects can be obtained.

When a two-dimensional tomogram is to be displayed, this ultrasonic diagnostic apparatus visualizes motion information associated with a direction orthogonal to a tomogram by mapping it on the tomogram. This makes it possible to obtain display information which cannot be acquired in the prior art and determine shortening information and thickening information which are said to be orthogonal to each other and have different mechanisms. As a result, in image diagnosis of the heart, local cardiac muscle wall motion can be easily grasped, and diagnosis of myocardial infarction can be supported.

According to this ultrasonic diagnostic apparatus, for example, volume data associated with a TSI image of a diagnosis target is generated by interpolation processing using a TSI image of a long axis (short axis) view. Therefore, for example, shortening (thickening) information can be mapped on a two-dimensional image by only obtaining a plurality of long axis (a plurality of short axis) view, and shortening information and thickening information can be determined in a composite manner. This makes it unnecessary to obtain both a long axis view and a short axis view, and hence makes it possible to shorten the work time in image diagnosis, thereby reducing the burdens on the operator and the subject.

Second Embodiment

The second embodiment of the present invention will be described next. An ultrasonic diagnostic apparatus 10 according to this embodiment can simultaneously map and visualize shortening information and thickening information on an arbitrary tomogram.

Figure 14:
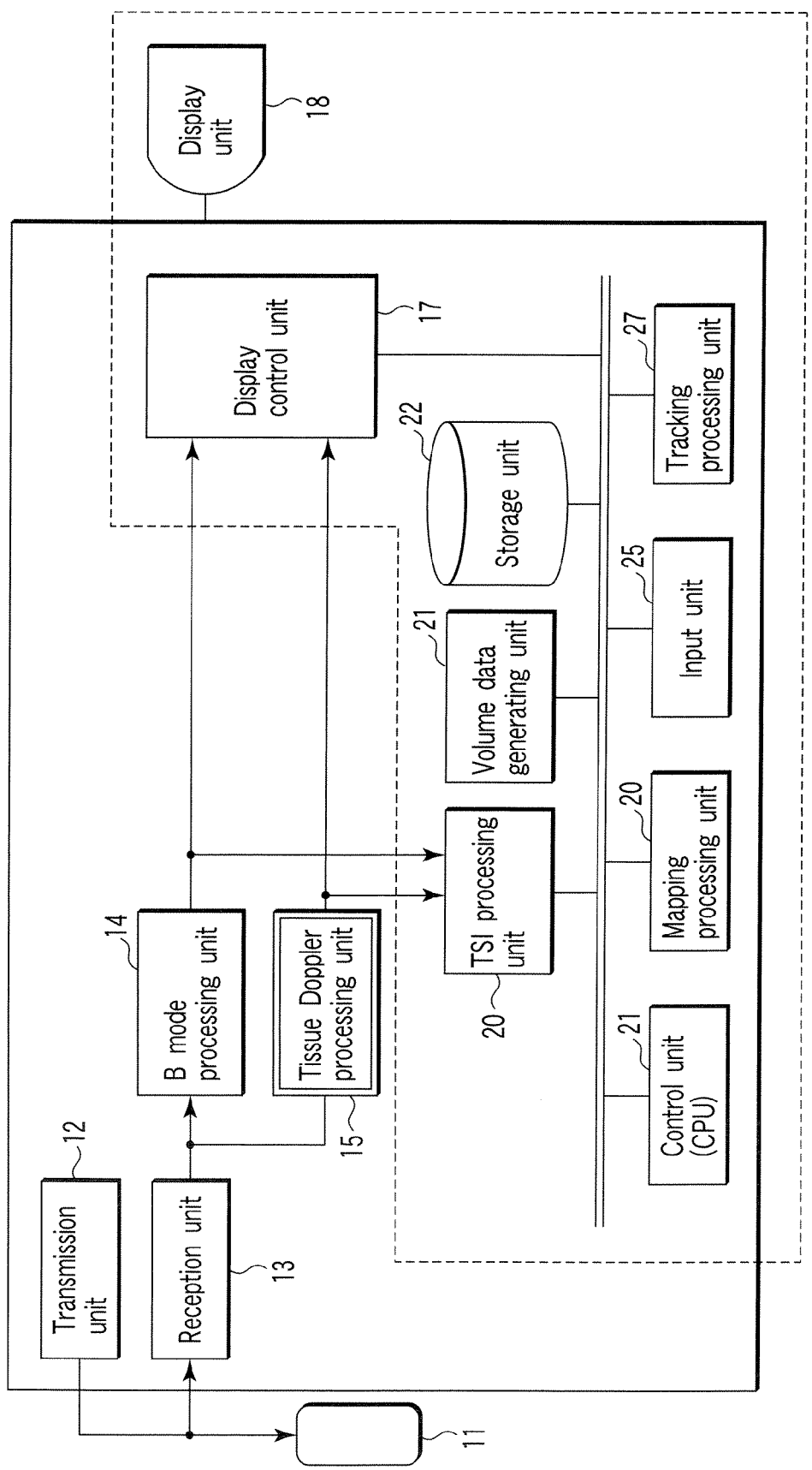
FIG. 14 is a block diagram showing the arrangement of an ultrasonic diagnostic apparatus 10 according to the second embodiment.

FIG. 14 is a block diagram showing the arrangement of an ultrasonic diagnostic apparatus 10 according to the second embodiment. This apparatus differs from the ultrasonic diagnostic apparatus 10 in FIG. 1 in that it further comprises a tracking processing unit 27. The tracking processing unit 27 computes thickening information and the like in the direction of the myocardial wall thickness by performing two-dimensional or three-dimensional speckle tracking (tracking processing) in a tissue image acquired for each time phase by, for example, B mode imaging.

FIG. 15 is a view for explaining the concept of mapping processing in this embodiment. As shown in FIG. 15, volume data V associated with a TSI image of a diagnosis target is generated by an existing method, and shortening information is computed by using the data.

An arbitrary short axis view E1 is designated, and thickening information in the wall direction is computed by speckle tracking of a monochrome image in the short axis slice. Concurrently with this operation, an arbitrary long axis view E2 is designated, and thickening information in the wall direction is computed by speckle tracking of a monochrome image in the long axis slice.

Mapping images F1 and F2 are then generated by performing color conversion upon assigning colors in accordance with motion such that red is assigned to an expansion component of the computed shortening information, blue is assigned to a contraction component, and green is assigned to a thickness increase component of the thickening information. Each of the generated mapping images is superimposed on a background monochrome image (short axis view or long axis view).

Figure 16:
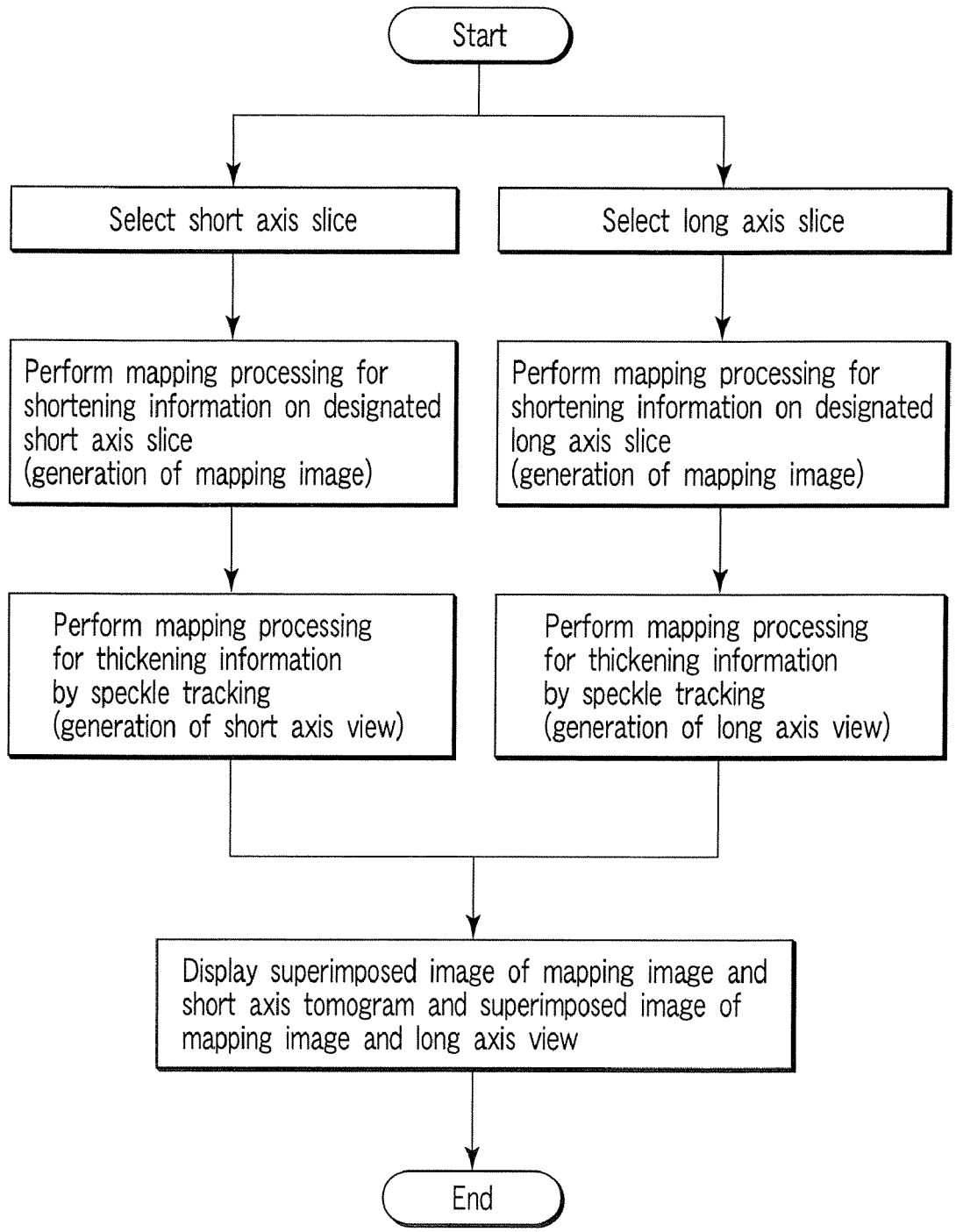
FIG. 16 is a flowchart showing the flow of mapping processing according to the second embodiment.

The flowchart of FIG. 16 shows the above sequence.

According to the above arrangement, a short axis image on which shortening information is mapped and a long axis view on which thickening information is mapped can be simultaneously displayed. Therefore, the observer can observe the thickening information and the shortening information on both the short axis view and the long axis view, and hence can easily grasp local myocardial motion in image diagnosis of the heart. This can suitably support diagnosis of myocardial infarction or the like.

Third Embodiment

The first and second embodiments have exemplified the case wherein thickening information and shortening information are used as motion information. However, motion information which can be used for the mapping function of an ultrasonic diagnostic apparatus of the third embodiment is not limited to thickening information or shortening information. This embodiment will exemplify a case wherein the mapping processing described in the first embodiment and the mapping processing described in the second embodiment are executed by using motion information other than thickening information and shortening information.

An ultrasonic diagnostic apparatus 10 according to this embodiment has substantially the same arrangement as that shown in FIG. 14. The mapping function using each motion information will be described below.

(Motion Information: Torsional Motion)

Figure 21:
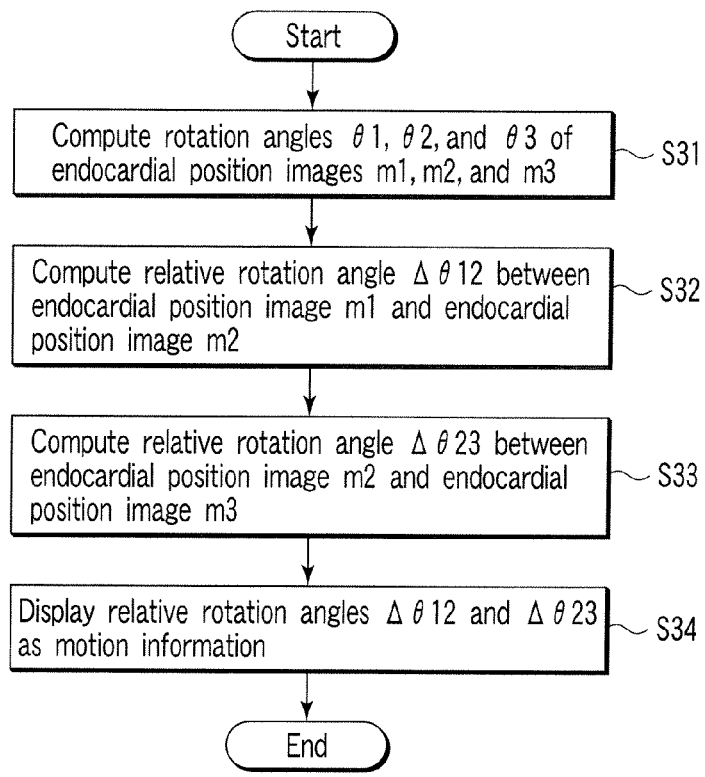
FIG. 21 is a flowchart showing the flow of mapping processing to be performed when torsional motion is used as motion information.
Figure 22:
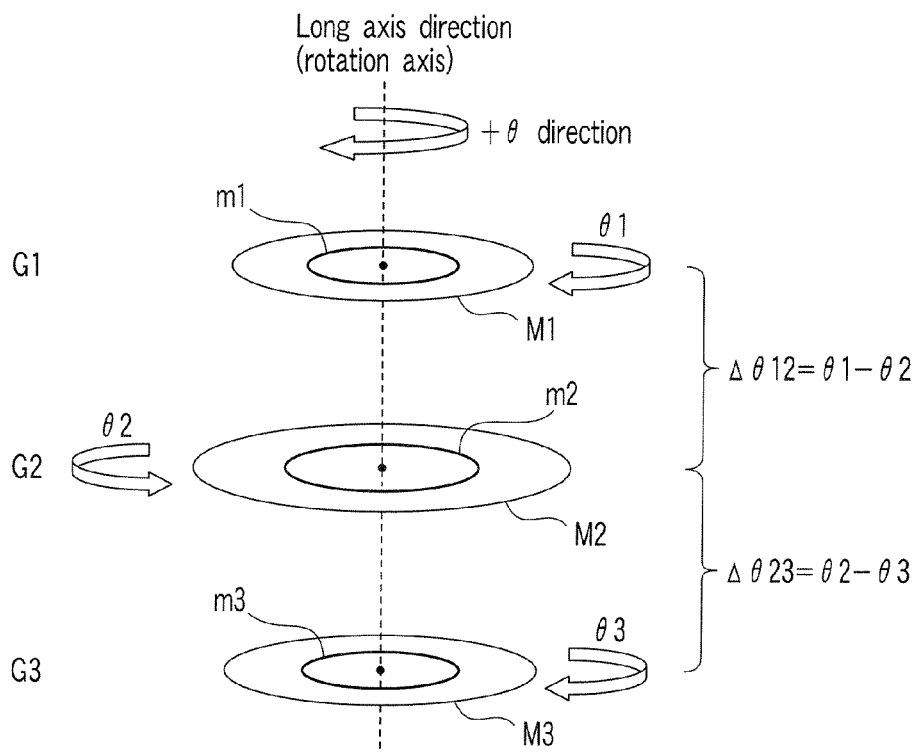
FIG. 22 is a view for explaining mapping processing to be performed when torsional motion is used as motion information.

A case wherein the state of the torsional motion of the cardiac wall is used as motion information will be described with reference to FIGS. 21 and 22. When a measurement image area is designated on a tomogram displayed on a display unit 18 (step S31), a tracking processing unit 27 computes the rotation angle (local motion information) of an endocardial position image m1 with its axis coinciding with a direction (the long axis direction of the heart) perpendicular to a slice of a apical short axis image G1 by executing two-dimensional tracking of the endocardial position image m1 using tomograms constituting a plurality of volume data along a time sequence. Likewise, for the papillary muscle short axis image G2 and the basal short axis image G3, the tracking processing unit 27 computes the rotation angles (local motion information) of endocardial position images m2 and m3 with their axes coinciding with the long axis direction of the heart (step S32). Note that the tracking processing unit 27 may compute epicardial position images M1, M2, and M3 instead of the endocardial position images m1, m2, and m3.

At this time, the tracking processing unit 27 computes the rotation angles of the endocardial position images m1, m2, and m3 as rotation angles corresponding to the time phase (reference time phase) in which the endocardial position image m1 is input in step S31. Alternatively, the rotation angles of the endocardial position images m1, m2, and m3 in adjacent frames (i.e., consecutive frames) may be sequentially computed along a time sequence.

The TSI processing unit 20 computes the difference (relative rotation angle) between the rotation angle of the endocardial position image m1 and the rotation angle of the endocardial position image m2 (step S33). Likewise, the TSI processing unit 20 computes the difference (relative rotation angle) between the rotation angle of the endocardial position image m2 and the rotation angle of the endocardial position image m3 (step S34).

The processing in steps S33 and S34 will be concretely described with reference to FIG. 22. With predetermined operation through the input unit 25, for example, the counterclockwise direction is defined as a positive rotation direction (+θ direction). In addition, the rotation angles of the endocardial position images m1, m2, and m3 are represented by θ1, θ2, and θ3, respectively.

A relative rotation angle Δθ12 computed in step S33 is calculated according to Δθ12=θ1−θ2 (or θ2−θ1). A relative rotation angle Δθ23 computed in step S34 is calculated according to Δθ23=θ2−θ3 (or θ3−θ2).

The relative rotation angle Δθ12 obtained in step S33 is information reflecting the state (magnitude) of torsional motion of the cardiac wall between the slice position of the apical short axis image G1 and the slice position of a papillary muscle short axis image G2. That is, when relative rotation angle Δθ12=0 (θ1=θ2), the cardiac wall rotates in the same direction through the same angle at arbitrary positions between these slice positions, and hence it can be regarded that there is no torsion in the rotation direction.

If |Δθ12|≠0, there is a rotation angle difference between these slice positions, and hence the cardiac wall has twisted in the rotational angle direction. The torsion of the cardiac wall increases as the relative rotation angle Δθ12 increases. For example, if the sign of θ1 differs from the sign of θ2, i.e., the rotation direction of the endocardial position image m1 is opposite to that of the endocardial position image m2, the absolute value of the relative rotation angle Δθ12 becomes relatively large.

Likewise, a relative rotation angle Δθ23 obtained in step S34 is information reflecting the magnitude of torsional motion of the cardiac wall between the slice position of the papillary muscle short axis image G2 and the slice position of a basal short axis image G3.

The mapping processing unit 24 sets the relative rotation angles Δθ12 and Δθ23 computed in steps S33 and S34 as motion information representing the magnitude of the torsional motion of the cardiac wall, and generates a mapping image by color-mapping the information on, for example, a long axis view. The display control unit 17 superimposes and displays this mapping image on a mapping image on which a morphological image of the tissue or predetermined motion information is mapped (step S35). Referring to the displayed relative rotation angles Δθ12 and Δθ23 allows the user to grasp the magnitude of the torsional motion of the cardiac wall. In this case, the relative rotation angles of the endocardium and epicardium of the cardiac wall can be computed, and the magnitude of torsional motion can be evaluated on the basis of the two relative rotation angles (for example, the average value of the two relative rotation angles is calculated).

The velocity of the torsional motion of the cardiac wall between the endocardial position images m1 and m2 can be obtained by differentiating the relative rotation angle Δθ12 with time. Likewise, the velocity of the torsional motion of the cardiac wall between the endocardial position images m2 and m3 can be obtained by differentiating the relative rotation angle Δθ23 with time. These velocities can be displayed on a display unit 18. Assume that in this case, "differentiation" includes processing of performing general differentiation computation and dividing the relative rotation angles by the time interval between frames in which the relative rotation angles are obtained.

(Motion Information: Relative Rotation Gradient)

Figure 23:
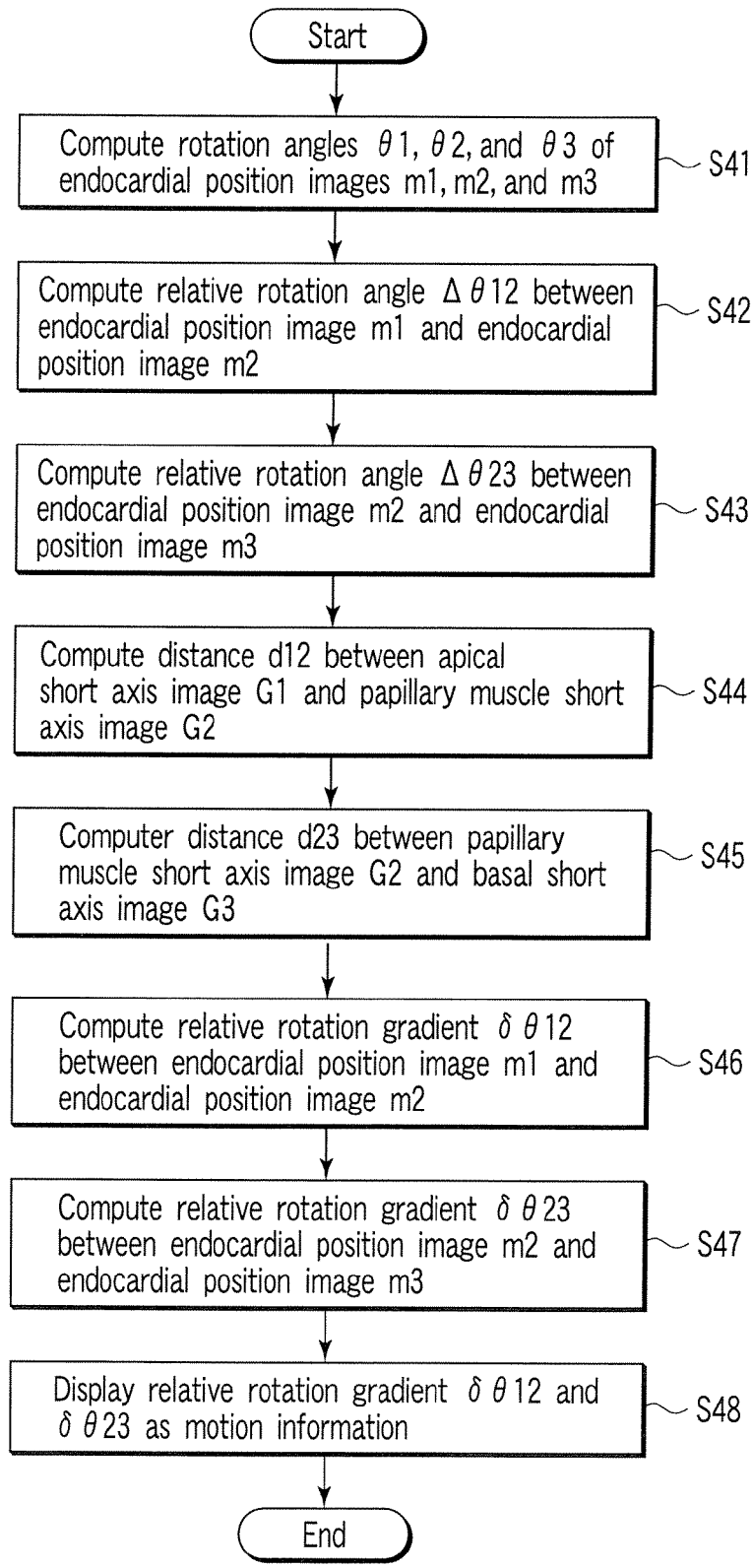
FIG. 23 is a flowchart showing the flow of mapping processing to be performed when a relative rotation gradient is used as motion information.

Processing to be performed when the relative rotation gradient of the cardiac wall is acquired as motion information will be described with reference to FIGS. 23 and 24. This relative rotation gradient is motion information indicating the degree of the torsional motion of the cardiac wall.

The tracking processing unit 27 computes the rotation angle θ1 of the endocardial position image m1 of the apical short axis image G1, the rotation angle θ2 of the endocardial position image m2 of the papillary muscle short axis image G2, and the rotation angle θ3 of the endocardial position image m3 of the basal short axis image G3 (step S41).

The tracking processing unit 27 computes the relative rotation angle Δθ12 between the rotation angle θ1 of the endocardial position image m1 and the rotation angle θ2 of the endocardial position image m2 (step S42), and computes the relative rotation angle Δθ23 between the rotation angle θ2 of the endocardial position image m2 and the rotation angle θ3 of the endocardial position image m3 (step S43).

The tracking processing unit 27 computes a distance d12 between the apical short axis image G1 and the papillary muscle short axis image G2 (step S44), and computes a distance d23 between the papillary muscle short axis image G2 and the basal short axis image G3 (step S45). The distances d12 and d23 can be computed on the basis of, for example, the coordinates of the slice positions of the cardiac apex short axis image G1, papillary muscle short axis image G2, and base short axis image G3 which are obtained by the control unit 23 after step S06.

Figure 24:
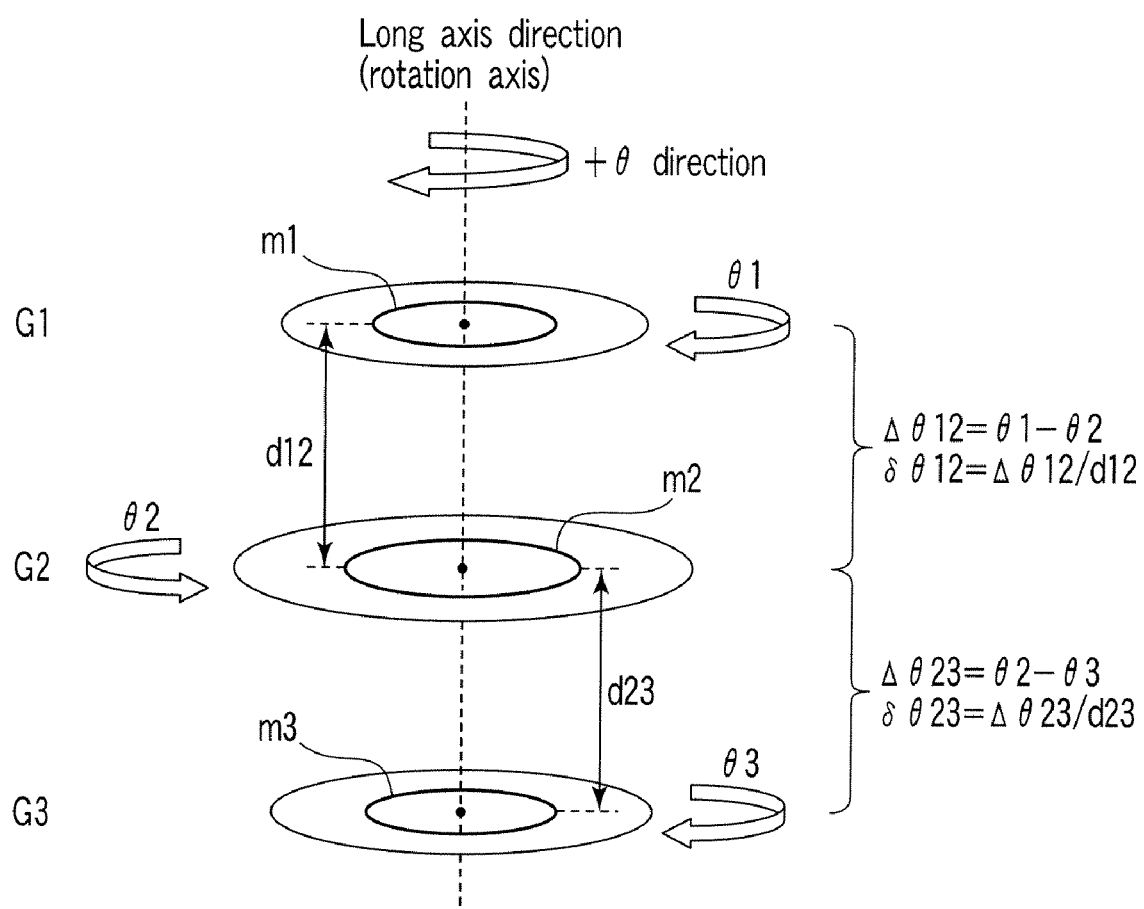
FIG. 24 is a view for explaining mapping processing to be performed when a relative rotation gradient is used as motion information.

As shown in FIG. 24, the TSI processing unit 20 computes relative rotation gradient δθ12=Δθ12/d12 between the endocardial position image m1 and the endocardial position image m2 by dividing the relative rotation angle Δθ12 obtained in step S42 by the distance d12 obtained in step S44 (step S46). Likewise, the TSI processing unit 20 computes relative rotation gradient δθ23=Δθ23/d23 between the endocardial position image m2 and the endocardial position image m3 by dividing the relative rotation angle Δθ23 obtained in step S43 by the distance d23 obtained in step S45 (step S47).

The TSI processing unit 20 sets the relative rotation gradients δθ12 and δθ23 computed in steps S46 and S47 as motion information representing the degree of the torsional motion of the cardiac wall, and generates a mapping image by color-mapping the motion information on, for example, a long axis view. The display control unit 17 superimposes and displays this mapping image on a mapping image on which the morphological image of the tissue or predetermined motion information is mapped (step S48).

The relative rotation gradient δθ12 indicates the magnitude of torsion per unit distance between the endocardium at the apex level and the endocardium at the papillary muscle level. The relative rotation gradient δθ23 indicates the magnitude of torsion per unit distance between the endocardium at the papillary muscle level and the endocardium at the basal level. That is, the relative rotation gradients δθ12 and δθ23 are motion information reflecting the degree of the torsion of the cardiac wall (endocardium). Referring to the displayed relative rotation gradients δθ12 and δθ23 allows the user to grasp the degree of the torsional motion of the cardiac wall. In this case, the relative rotation gradients of the endocardium and epicardium of the cardiac wall can be computed, and the degree of torsional motion can be evaluated on the basis of the two relative rotation gradients (for example, the average value of the two relative rotation gradients is calculated).

(Motion Information: Strain in Long Axis Direction)

Figure 25:
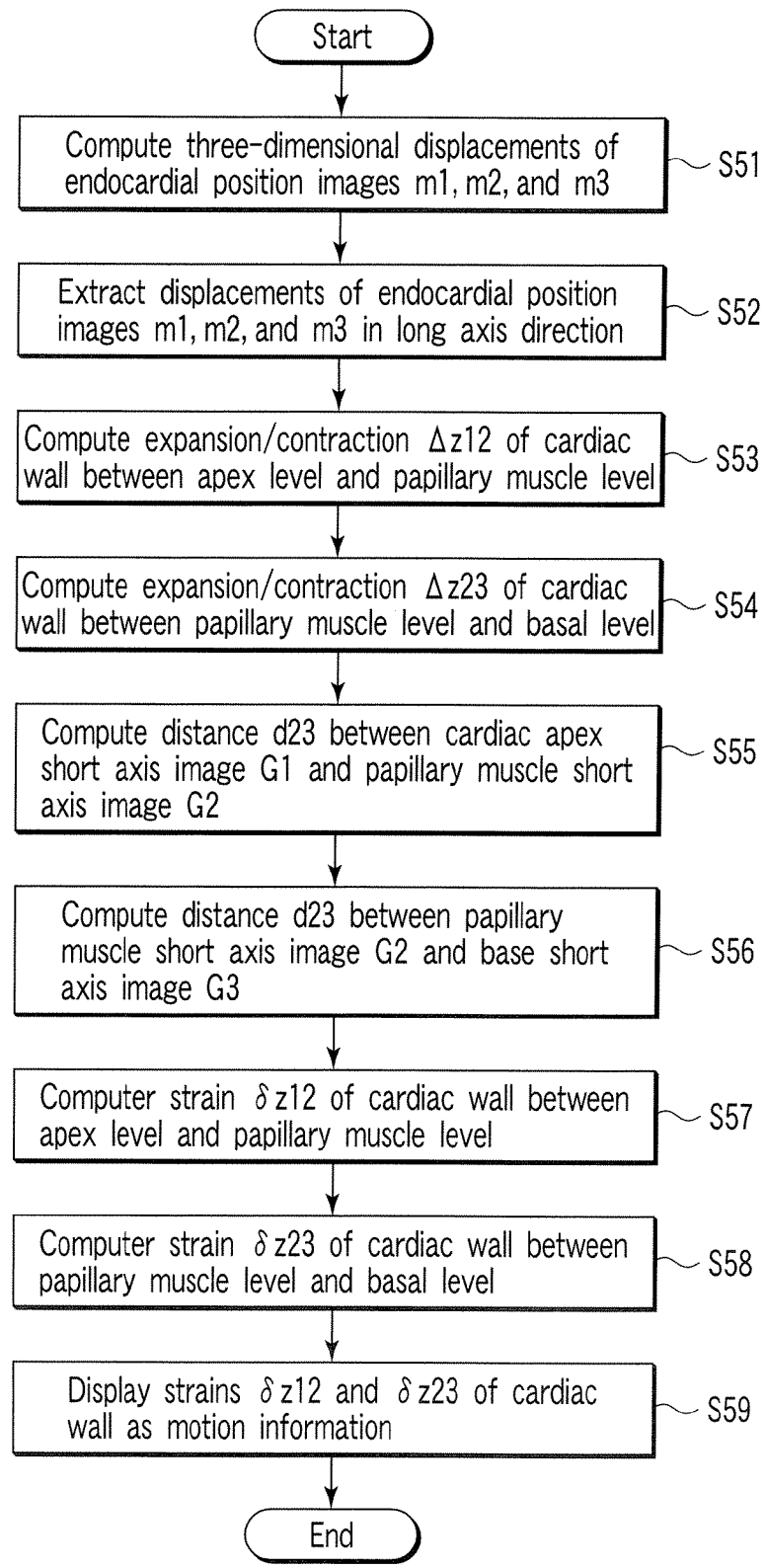
FIG. 25 is a flowchart showing the flow of mapping processing to be performed when a strain in the long axis direction is used as motion information.
Figure 26:
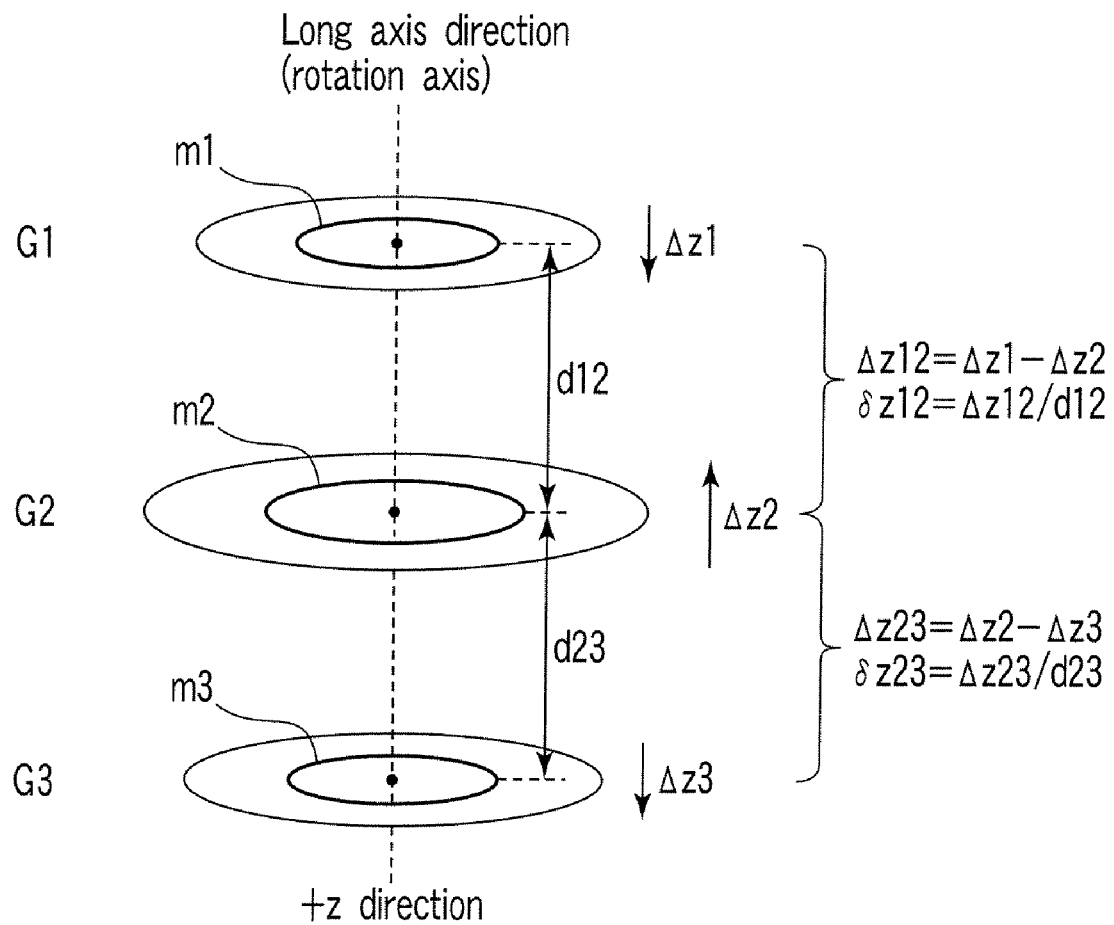
FIG. 26 is a view for explaining mapping processing to be performed when a strain in the long axis direction is used as motion information.

Processing to be performed when the strain of the cardiac wall in the long axis direction is acquired as motion information will be described with reference to FIGS. 25 and 26. This strain is information indicating the degree of the magnitude of the strain of the cardiac wall, and indicates the strain state of the cardiac wall.

First of all, the tracking processing unit 27 computes three-dimensional displacements (Δx1, Δy1, Δz1), (Δx2, Δy2, Δz2), and (Δx3, Δy3, Δz3) of a tomogram on which a measurement image area is designated with respect to the endocardial position image m1, endocardial position image m2, and endocardial position image m3 (step S51), and extracts the displacements Δz1, Δz2, and Δz3 in the Z direction (long axis direction) from these three-dimensional displacements (step S52).

The tracking processing unit 27 computes expansion/contraction Δz12=Δz1−Δz2 of the cardiac wall between the apex level and the papillary muscle level (step S53), and computes expansion/contraction Δz23=Δz2−Δz3 of the cardiac wall between the papillary muscle level and the basal level (step S54).

With regard to the apical short axis image G1, papillary muscle short axis image G2, and basal short axis image G3 on which measurement image areas are designated, the tracking processing unit 27 computes a distance d12 between the cardiac apex short axis image G1 and the papillary muscle short axis image G2 (step S55), and computes a distance d23 between the papillary muscle short axis image G2 and the basal short axis image G3 (step S56).

The TSI processing unit 20 computes strain $\delta z12 = \Delta z12/d12$ in the long axis direction between the apex level and the papillary muscle level by dividing the expansion/contraction $\Delta z12$ computed in step S53 by the distance d12 computed in step S45 (step S57). The TSI processing unit 20 also computes strain $\delta z23 = \Delta z23/d23$ in the long axis direction between the papillary muscle level and the basal level by dividing the expansion/contraction $\Delta z23$ computed in step S44 by the distance d23 computed in step S46 (step S58).

The TSI processing unit 20 sets the strains $\delta z12$ and $\delta z23$ of the cardiac wall computed in steps S57 and S58 as motion information representing the magnitude of the strain of the cardiac wall, and generates a mapping image by color-mapping the motion information on, for example, a short axis view. The display control unit 17 superimposes and displays this mapping image on a mapping image on which a morphological image of the tissue or predetermined motion information is mapped (step S59). Referring to the displayed strains $\delta z12$ and $\delta z23$ of the cardiac wall allows the user to grasp the magnitude of the strain of the cardiac wall.

Note that the strains of the endocardium and epicardium of the cardiac wall can be computed, and the magnitude of the strain can be evaluated on the basis of the two strain values (for example, the average value of the two strain values is calculated).

(Motion Information: Strain Rate in Long Axis Direction)

Processing to be performed when the strain rate of the cardiac wall in the long axis direction is acquired as motion information will be described. This strain rate is information indicating the temporal change rate of the strain of the cardiac wall, and indicates the strain state of the cardiac wall.

When a strain rate is to be obtained, the strain $\delta z12$ in the long axis direction between the apex level and the papillary muscle level and the strain $\delta z23$ between the papillary muscle level and the basal level are computed by performing the same processing as that in steps S51 to S58 in the flowchart of FIG. 24.

In this case, the strains $\delta z12$ and $\delta z23$ are computed with respect to the apical short axis image G1, papillary muscle short axis image G2, and basal short axis image G3 in two time phases t1 and t2. The TSI processing unit 20 computes a strain rate in the long axis direction between the apex level and the papillary muscle level by dividing the strain $\delta z12$ by time interval $\Delta t$ $\Delta t = |t1-t2|$. The TSI processing unit 20 also computes a strain rate in the long axis direction between the papillary muscle level and the basal level by dividing the strain $\delta z23$ by the time interval $\Delta t$. Note that a strain rate may be calculated from a strain by executing general differentiation computation.

The TSI processing unit 20 sets strain computed rates $\delta z12/\Delta t$ and $\delta z23/\Delta t$ of the cardiac wall as motion information representing the temporal change rate of the strain of the cardiac wall, and generates a mapping image by color-mapping the motion information on, for example, a short axis view. The display control unit 17 superimposes and displays this mapping image on a mapping image on which a morphological image of the tissue or predetermined motion information is mapped. Referring to the displayed strain rates of the cardiac wall allows the user to grasp the temporal change rate of the strain of the cardiac wall.

Note that the strain rates of the endocardium and epicardium of the cardiac wall can be computed, and the temporal change rate of the strain can be evaluated on the basis of the two strain rates (for example, the average value of the two strain rates is calculated).

According to the above arrangement, even if motion information other than thickening information and shortening information is used, the mapping processing described in the first embodiment and the mapping processing described in the second embodiment can be realized.

The present invention is not limited to the above embodiments, and constituent elements can be modified and embodied in the execution stage within the spirit and scope of the invention. The following are concrete modifications.

(1) Each embodiment described above is configured to display a mapping image while superimposing it on a monochrome image of a slice. In contrast to this, a mapping image may be generated by mapping both thickening information and shortening information on one short axis view or long axis view, and may be displayed. In this case, for example, as shown in FIG. 17, different hues may be assigned to the thickening information and the shortening information, and the pieces of information may be displayed in gray levels corresponding to the intensities of the strains.

Figure 19:
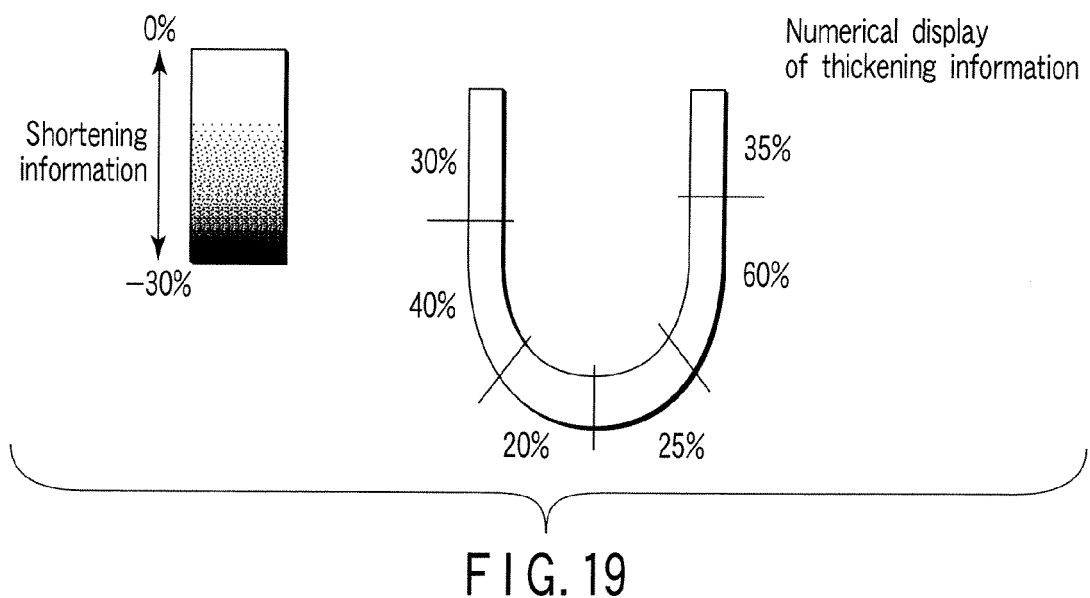
FIG. 19 is a view showing a modification of the display form of thickening information and shortening information in a mapping image.

(2) Each embodiment described above is configured to generate and display a mapping image for hue-displaying thickening information and shortening information. In contrast to this, as shown in FIGS. 18 and 19, a cardiac tissue on a mapping image may be divided into small areas, and motion information in each of the small areas may be converted into a numerical value and displayed.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

(3) For a concrete explanation, each embodiment described above has exemplified the case wherein the volume data of a TSI image associated with a diagnosis target is generated by using the volume data acquired by three-dimensional scanning or the like, and orthogonal mapping processing is performed by using the generated volume data. However, orthogonal mapping processing does not always require the volume data of a TSI image associated with a diagnosis target. That is, it suffices for this orthogonal mapping processing if there is image data from which motion information in a direction orthogonal to a slice can be acquired at each point on the tissue displayed on a short axis view or long axis view selected for the generation of a mapping image.

Figure 20:
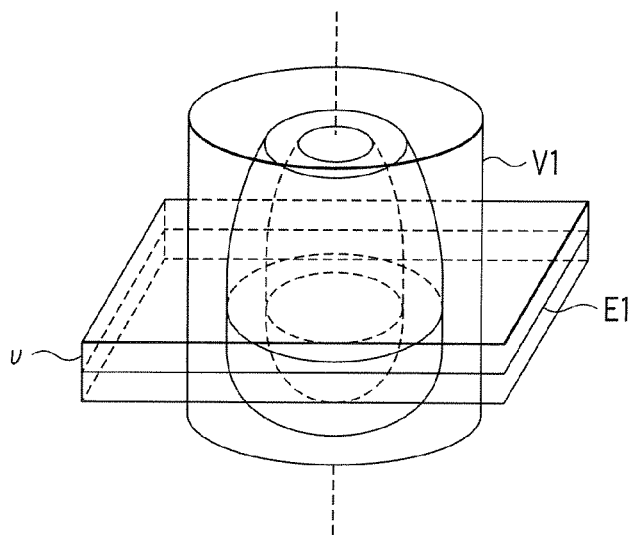
FIG. 20 is a view for explaining a modification of an embodiment of the present invention.

For example, as shown in FIG. 20, therefore, this orthogonal mapping processing can also be realized by using image data v including the tomogram E1 selected for the generation of a mapping image and has a predetermined thickness in a direction orthogonal to the tomogram. When this image data v is to be acquired, it suffices to acquire a plurality of tomograms substantially orthogonal to the tomogram E1 and perform the above interpolation processing or perform ultrasonic scanning on an area corresponding to at least the image data v.

(4) Each embodiment described above has exemplified the use of a TSI image. However, the present invention is not limited to this, and this orthogonal mapping processing can be applied to any image associated with the motion information of a tissue. Therefore, this orthogonal mapping processing can be executed by using, for example, a tissue Doppler image, and the same effects as those described above can be obtained.

(5) Each embodiment described above has exemplified the case wherein a mapping image obtained by mapping processing is superimposed and displayed on another image. However, the present invention is not limited to this, and a projection image (e.g., a volume rendering image, a surface rendering image, or a developed image based on polar coordinates or the like) may be generated and displayed by using a plurality of mapping images obtained by mapping processing.

What is claimed is:

1. An ultrasonic diagnostic apparatus comprising:
a storage unit that stores an image data set;
a motion information generating unit which generates motion information of a tissue along a first direction based on said data set;
a two-dimensional image generating unit which generates a two-dimensional image associated with a plane of said data set which is not parallel to the first direction;
a mapping image generating unit which generates a mapping image by mapping the motion information of the tissue along the first direction at a plurality of positions on the two-dimensional image; and
a display unit which displays the mapping image.

2. An apparatus according to claim 1, wherein
the motion information generating unit generates motion information associated with three-dimensional motion of a tissue, and
the two-dimensional image generating unit generates the two-dimensional image from three-dimensional data associated with a morphology of the tissue.

3. An apparatus according to claim 1, wherein
the motion information generating unit generates motion information along a long axis direction of a cardiac tissue on a short axis slice of the heart, and
the two-dimensional image generating unit generates a two-dimensional image associated with the short axis slice.

4. An apparatus according to claim 1, wherein
the motion information generating unit generates motion information along a short axis direction of a cardiac tissue on a long axis slice of the heart, and
the two-dimensional image generating unit generates a two-dimensional image associated with the long axis slice.

5. An apparatus according to claim 1, wherein the motion information is one of information associated with torsional motion of a cardiac tissue, information associated with a relative rotation gradient of the cardiac tissue, information associated with a strain or strain rate of the cardiac tissue, and information associated with a displacement of the cardiac tissue.

6. An apparatus according to claim 1, wherein the motion information generating unit generates one of three-dimensional motion information generated by three-dimensionally scanning a subject to be examined and motion information generated by interpolation processing based on a plurality of two-dimensional scannings.

7. An apparatus according to claim 1, wherein the display unit displays the mapping image in color mapping in which a predetermined color luminance is assigned so as to correspond a degree of motion determined by the motion information.

8. An apparatus according to claim 1, wherein the display unit divides a cardiac tissue on the mapping image into small areas, converts motion information in each of the small areas into a numerical value, and displays the numerical value.

9. An apparatus according to claim 1, wherein
the two-dimensional image generating unit generates two-dimensional images associated with a plurality of planes which are not parallel to the first direction,
the mapping unit generates a plurality of mapping images by mapping the motion information on the two-dimensional images associated with said plurality of planes, and
the display unit generates and displays a projection image based on said plurality of mapping images.

10. An ultrasonic image processing method comprising:
generating motion information of a tissue along a first direction;
generating a two-dimensional image associated with a plane which is not parallel to the first direction;
generating a mapping image by mapping the motion information of the tissue along the first direction at a plurality of positions on the two-dimensional image; and
displaying the mapping image.

11. A method according to claim 10, wherein
in the motion information generating, motion information associated with three-dimensional motion of the tissue is generated, and
in the two-dimensional imaging generating, the two-dimensional image is generated from three-dimensional data associated with a morphology of the tissue.

12. A method according to claim 10, wherein
in the motion information generating, motion information along a long axis direction of a cardiac tissue on a short axis slice of the heart is generated, and
in the two-dimensional image generating, a two-dimensional image associated with the short axis slice is generated.

13. A method according to claim 10, wherein
in the motion information generating, motion information along a short axis direction of a cardiac tissue on a long axis slice of the heart is generated, and
in the two-dimensional image generating, a two-dimensional image associated with the long axis slice is generated.

14. A method according to claim 10, wherein the motion information is one of information associated with torsional motion of a cardiac tissue, information associated with a relative rotation gradient of the cardiac tissue, information associated with a strain or strain rate of the cardiac tissue, and information associated with a displacement of the cardiac tissue.

15. A method according to claim 10, wherein in the motion information generating, one of three-dimensional motion information generated by three-dimensionally scanning a subject to be examined and motion information generated by interpolation processing based on a plurality of two-dimensional scannings is generated.

16. A method according to claim 10, wherein in the displaying, the mapping image is displayed in color mapping in which a predetermined color luminance is assigned so as to correspond a degree of motion determined by the motion information.

17. A method according to claim 10, wherein in the displaying, a cardiac tissue on the mapping image is divided into small areas, motion information in each of the small areas is converted into a numerical value, and the numerical value is displayed.

18. A method according to claim 10, wherein
in the two-dimensional image generating, two-dimensional images associated with a plurality of planes which are not parallel to the first direction are generated, in the mapping, a plurality of mapping images are generated by mapping the motion information on the two-dimensional images associated with said plurality of planes, and in the displaying, a projection image is generated and displayed on the basis of said plurality of mapping images.

19. An apparatus according to claim 1, wherein that the motion information generating unit generates motion information of a heart tissue.

20. A method according to claim 10, wherein that the motion information is associated with a heart tissue.

* * * * *